United States Patent [19]

Parks

[11] Patent Number: 4,479,798

[45] Date of Patent: Oct. 30, 1984

[54] SUBCUTANEOUS IMPLANT USEFUL IN EFFECTING HYPERTHERMIC TREATMENT

[75] Inventor: Leon C. Parks, Baltimore, Md.

[73] Assignee: Research Against Cancer, Inc., Jackson, Miss.

[21] Appl. No.: 212,750

[22] Filed: Dec. 4, 1980

Related U.S. Application Data

[62] Division of Ser. No. 068,950, Aug. 23, 1979, , which is a division of Ser. No. 802,033, May 3, 1971, Pat. No. 4,181,132.

[51] Int. Cl.$^3$ .............................................. A61M 1/03
[52] U.S. Cl. ........................................ 604/175; 604/4
[58] Field of Search ............ 128/214 R, 214.4, 214 B, 128/347, 348, DIG. 26, 399; 604/4, 175

[56] References Cited

U.S. PATENT DOCUMENTS

| | | | |
|---|---|---|---|
| 958,854 | 5/1910 | Bunn . | |
| 2,815,257 | 7/1974 | Buselmeier | 128/214 |
| 3,064,649 | 11/1962 | Fuson | 128/214 |
| 3,241,602 | 3/1966 | Andreassen | 165/26 |
| 3,638,649 | 2/1972 | Ersek | 128/214 |
| 3,640,340 | 2/1972 | Leonard | 165/166 |
| 3,713,441 | 1/1973 | Thomas | 128/214 |
| 3,765,032 | 10/1973 | Palma . | |
| 3,783,868 | 1/1974 | Bokros | 128/348 X |
| 3,853,126 | 12/1974 | Schulte | 128/348 X |
| 3,982,535 | 9/1976 | Bahrton | 128/214 |
| 3,991,756 | 11/1976 | Synder | 128/214 |
| 3,998,222 | 12/1976 | Shihata | 128/214 R |

FOREIGN PATENT DOCUMENTS

| | | | |
|---|---|---|---|
| 1114281 | of 1962 | Fed. Rep. of Germany . | |
| 64842 | of 1967 | Fed. Rep. of Germany . | |
| 1556620 | 10/1970 | Fed. Rep. of Germany | 128/399 |
| 1140895 | 8/1957 | France | 128/399 |
| 1551454 | of 1968 | France . | |
| 1521064 | 4/1968 | France | 128/399 |
| 244467 | 9/1946 | Switzerland | 128/347 |
| 538713 | of 1976 | U.S.S.R. . | |

OTHER PUBLICATIONS

Proceedings of the International Symposium on Cancer Therapy by Hyperthermia & Radiation, held Apr. 28–30, 1975, in Washington, D.C.
Effect of Hyperthermia on the Radiosensitivity of Normal and Malignant Cells in Mice, K. G. Hofer et al., Cancer, 38:279, 1976.
(List continued on next page.)

*Primary Examiner*—Michael H. Thaler
*Attorney, Agent, or Firm*—Cushman, Darby & Cushman

[57] ABSTRACT

A process of hyperthermic treatment of a patient which comprises the steps of establishing a sterile extracorporeal flow path for blood having an inlet, an outlet and a temperature control zone therebetween, establishing communication of the flow path inlet with the patient's bloodstream so that blood can be supplied to the extracorporeal flow path without adversely affecting the blood circulation in the area from which the blood is withdrawn, establishing communication of the flow path outlet with the patient's bloodstream so that blood is returned to the bloodstream in such a way as to be distributed systemically, pumping blood withdrawn from the patient's bloodstream through the temperature control zone at a controlled rate of at least approximately 1 liter per minute and returning the same to the patient's bloodstream to be distributed systemically, controlling the temperature of the blood flowing through the temperature control zone for an initial period during which the temperature level of the blood within the zone is raised without subjecting the same to localized temperatures in excess of approximately 45° C. so that the systemic distribution of the returned blood gradually increases the core temperature of the patient's body to a generally stable temperature condition at a level of approximately 41.5° C. but not higher than approximately 42.5° C., and maintaining control of the temperature of the blood flowing through the temperature control zone at the generally stable temperature for a second time period sufficient to effect the desired treatment and apparatus for carrying out the method.

16 Claims, 11 Drawing Figures

OTHER PUBLICATIONS

Total Body Hyperthermia and Preliminary Results in Human Neoplasmus, J. M. Larkin et al., Sur. Forum, 27:121, 1976.

Exploiting Heat Sensitivity of Leukemic Cells, T. E. Wheldon, Lancet, 1:1363, 1976.

Hyperthermia in the Treatment of the Cancer Patient, Cancer, 37:2075–2983, 1976.

Induction of Controlled Hyperthermia in Treatment of Cancer, M. A. Henderson et al., Lancet, 1:1275.

Selective Heat Sensitivity of Cancer Cells, Cancer, 20–1351, 1967.

Clinical Effects of Whole-Body Hyperthermia in Advanced Malignancy, Pettigrew, British Medical Journal, 1974, 4, 679–682.

Fig. 2

SUBCUTANEOUS IMPLANT USEFUL IN EFFECTING HYPERTHERMIC TREATMENT

This application is a division of application Ser. No. 68,950 filed Aug. 23, 1979, which is a division of Ser. No. 802,033, filed May 31, 1977, now U.S. Pat. No. 4,181,132, issued Jan. 1, 1980.

This invention relates to hyperthermia, and more particularly to improved method and apparatus for effecting hyperthermic treatment specifically for the purpose of retarding the growth of growing cancer cells.

There is mounting evidence that the application of heat within the range of 41.5° C. to 43.0° C. can be used effectively to retard the growth of cancer cells.

Recent interest in this subject has intensified to the extent that an International Symposium on Cancer Therapy by Hyperthermia and Radiation was held in Washington, D.C. in April of 1975 under the joint sponsorship of The National Cancer Institute of the U.S. Public Health Service and The American College of Radiology, in cooperation with the University of Maryland School of Medicine.

The Proceedings of this symposium are transcribed in a three hundred and four page volume containing many articles dealing with varied aspects of hyperthermia and cancer. These articles and the cited references thereof represent a comprehensive listing of available literature publications. For purposes of background, the articles contained in the Proceedings are hereby incorporated by reference into the present specification.

Other articles of interest since 1975, the date of the symposium, are as follows:

Hofer, K. G., Choppin, D. A. and Hofer, M. G.: Effect of Hyperthermia on the Radiosensitivity of Normal and Malignant Cells in Mice. Cancer, 38:279, 1976.

Larkin, J. M., Edwards, W. S. and Smith, D. E.: Total Body Hyperthermia and Preliminary Results in Human Neoplasmus. Surg. Forum, 27:121, 1976.

Wheldon, T. E.: Exploiting Heat Sensitivity of Leukemic Cells. Lancet, 1:1363, 1976.

Hyperthermia in the Treatment of the Cancer Patient. Cancer, 37:2075-2983, 1976.

Much of the above literature includes reports to the effect that hyperthermia utilized in a range of temperatures between 41.5° C. and 43.0° C. causes specific anticancer effects when used either as a primary or adjuvant agent against a wide spectrum of malignant disease. The literature indicates that hyperthermia has been shown to induce cytotoxicity in sarcoma and melanoma cells in tissue culture (Stehlin et al.) and strongly enhance antitumor effects of irradiation in vivo of L-1210 and Erlich ascites cells (Hofer et al.). The addition of hyperthermia to regional perfusion chemotherapy of melanoma resulted in an increased incidence of tumor control and patient survival without increased adverse effects (Stehlin et al.). Employed as a systemic agent, hyperthermia induced objective regression in 13 of 18 (70%) patients with disseminated disease resistant to other therapy, six of whom were surviving 11 to 22 months post treatment (Larkin et al.).

Experimental work undertaken in contemplation of the present invention indicates the effectiveness of hyperthermia against systemic disease may be even greater than indicated by Larkin et al. Although the levels of hyperthermia employed by Larkin et al. (approximately 42.0° C.) were adequate, the period of application was only five hours. Moreover, the procedures undertaken to effect the hyperthermic treatment would indicate that a stable temperature level of 42° C. was not maintained systemically for five hours. Larkin et al. employed insulating sheets and liquid heating blankets surrounding the patients for heat application. Due to the relatively poor conductivity of the skin and the further adverse effect to conductivity of profuse sweating, elevated systemic temperatures cannot be rapidly induced. Moreover, this adverse conductivity condition can be expected to maintain the existence of large temperature differentials throughout the system. For example, blanket control temperatures of 120° F. (48.89° C.) were utilized, a lethal systemic level.

Based upon the analysis of the type of problems enunciated above which are evident from the systemic procedures and devices heretofore proposed and utilized, a set of desirable criteria for method and devices for effecting hyperthermic treatment can be listed as follows:

1. Systemic temperatures of 41.5° to 43.0° C. induced.
2. Selected temperatures obtained within one hour.
3. Hyperthermia maintained for 24 to 48 hours.
4. Fine temperature control and potential autoregulation of temperature possible.
5. A rapid cooling as well as a heating effect readily achieved.
6. General anesthesia unnecessary or required for only a brief period.
7. Patients undergoing hyperthermic treatment maintained in a setting conductive to conventional care.
8. Hyperthermia possible in diverse settings such as radiation therapy or isolation areas.
9. Repetitious induction of courses of hyperthermia over a several day period possible.
10. Hyperthermia induced with reasonable safety in neutropenic or thrombocytopenic patients.

It is an object of the present invention to provide a method and apparatus for effecting hyperthermic treatment which will meet the above-listed desirable criteria. In accordance with the procedural principles of the present invention, this objective is obtained by establishing a sterile extracorporeal flow path for blood having an inlet, an outlet and a temperature control zone therebetween, establishing communication of the inlet of the extracorporeal flow path with the patient's bloodstream so that blood can be withdrawn and supplied to the extracorporeal flow path without adversely affecting the blood depleted areas from which the blood is withdrawn, establishing communication of the outlet of the extracorporeal flow path with the patient's bloodstream so that blood flowing from the extracorporeal flow path is returned to the bloodstream in such a way as to be distributed systemically, pumping blood withdrawn from the patient's bloodstream along the extracorporeal flow path through the temperature control zone at a controlled rate and returning the same to the patient's bloodstream to be distributed systemically, as aforesaid, controlling the temperature of the blood flowing along the extracorporeal flow path through the temperature control zone for an initial period during which the temperature level of the blood within the zone is raised without subjecting the same to localized temperatures in excess of approximately 45° C. so that the systemic distribution of the returned blood gradually increases the core temperature of the patient's body to a generally stable temperature condition at a level of approximately 41.5° C., but not higher than approximately 42.5° C., and maintaining control of the temperature of the blood flowing along the extracorporeal flow path through the temperature control zone at the generally stable temperature condition for a second time period sufficient to retard the growth of cancer cells.

It is recognized that extracorporeal heating of blood for anti-cancer purposes has been undertaken in regional perfusion practices. Procedures of this type are discussed by Cavaliere et al. and Stehlin and are to be distinguished from the systemic hyperthermia induced by the present procedures, as indicated above. In these regional perfusion practices, the main femoral artery and vein are temporarily occluded by vacular clamps or tourniquets and a closed extracorporeal system is established, solely within the femoral extremity. In this extracorporeal circuit, heat is applied as an adjunct to the other treatments, such as chemotherapy, which are utilized in the regional circulating system. This system necessitates the utilization of oxygenating equipment of a type similar to that used in open heart surgery. As is evident from the known time limitations imposed upon open hert surgery by viture of the utilization of oxygenating equipment, the time frame within which such combined oxygenating and heating treatments can be continued even on a regional basis without imposing at least a percentile permanent damage to the blocked femoral areas of the patient is quite limited.

Pettigrew, in referring to these regional perfusion practices as background to his preferred combined hot wax bath and heated respiratory gases procedure for inducing total body hyperthermia, appears to consider the regional perfusion procedures to be applicable to induce both regional hyperthermia as well as total body hyperthermia, perhaps by analogy to the open heart extracorporeal shunting. (Induction of Controlled Hyperthermia in Treatment of Cancer, Henderson, M. A. and Pettigrew, R. T. Lancet, 1:1275, 1971 and Cancer Therapy by Whole Body Heating, Pettigrew, R. T. Proceedings, p. 282). The Pettigrew Lancet article characterized the regional perfusion work of Cavaliere et al. ("Selective Heat Sensitivity of Cancer Cells", Cancer, 1967, 20-1351) as having "achieved very satisfactory temperatures in the malignancies using an arteriovenous shunt and a heat exchanger, but since this requires surgery it cannot be repeated indefinitely and can only be applied easily to peripheral malignancy."

It is of significance, however, to note that the recognized practitioners of regional perfusion, namely Cavaliere et al. and Stehlin et al., have both indicated that the regional perfusion practices utilizing a shunt and an extracorporeal heat exchanger are limited to regional extremity applications and both have utilized other procedures for inducing total body hyperthermia.

On page 135 of the cancer article Cavaliere et al. state:

"This method of high temperature treatment obviously has limitations and at present is indicated in patients with primary or recurrent malignant tumors of the limbs for whom the only alternative therapy would be amputation, which often does not prevent metastases. . . . It is evident that future progress in this field will come from total-body high-temperature treatment. We are now in the process of developing techniques towards this end, which are considerably different from those now being used."

The last paragraph of the Stehlin article in the Proceedings publication, page 271, sets forth the following:

"As a result of our experience with regional perfusion with heat, we are currently, and have for the past five years been investigating the possibility that systemic hyperthermia induced with bacterial toxins will enhance the antitumor effects of various chemotherapy agents on melanomas and sarcomas."

A preferred minimum flow rate in accordance with the principles of the present invention, is approximaterly 1 liter per minute. Such flow rate can be achieved by following the procedures of the present invention without affecting the femoral areas from which the blood is withdrawn. Thus, with the present procedure, there is no systemic femoral isolation as by a clamp or tourniquet occluding the main femoral artery and vein, but rather, a preferred procedure is to effect communication of the extracorporeal flow path between the femoral artery and the femoral vein through a side wall of each, so that systemic circulation in the femoral areas can continue. The pumping procedure undertaken to effect flow of the withdrawn blood through the temperature control zone of the extracorporeal flow path achieves an adequate controlled flow rate while permitting adequate systemic circulatory flow through the femoral areas sufficient to prevent the type of adverse effects over extended periods of time which will occur in the aforesaid regional perfusion techniques.

The present invention also contemplates an improved implantable device for facilitating the connection of the extracorporeal flow circuit with the blood system of the patient. Devices for establishing an extracorporeal blood flow path for the purposes of kidney dialysis as distinguished from systemic hyperthermic treatments are well-known. These devices, known as shunts, are made commercially available by several manufacturers. Typically, these shunt devices are implanted in the patient and include tubes which extend extracorporeally. These exteriorized tubes have caused considerable difficulty.

A good discussion of the difficulties encountered in the practices relating to such exteriorized shunt devices is contained in U.S. Pat. No. 3,998,222. In the opening paragraphs of the specification, one type of shunt device is described as a U-shaped loop, one end of which is connected to a vein and the other end of which is connected to an artery. The loop itself is implanted subcutaneously but outlet conduits extending from the sides of the loop protrude through open holes in the skin to outlet terminals on the outside of the body. Removable plugs fit in the outlet tubes and block the flow through these tubes during normal conditions. When the patient is subjected to dialysis, the plugs are removed and the outlet terminals are connected to inlet fittings for a dialysis machine. (See U.S. Pat. No. 3,826,257).

One of the problems enunciated in the opening paragraphs of the specification attributable to this type of exteriorized shunt is the risk of infection in the location where the outlets protrude through the opening holes in the skin. While there is considerable reference to problems relating to blood clotting in shunt devices of the prior art, there is proposed in the patent a shunt arrangement which would at least have the effect of alleviating the infection problem, in that the shunt device of the invention is arranged to be implanted in a completely interiorized or totally subcutaneous condition. In order to effect communication of the totally interiorized shunt device with the extracorporeal flow path, the implanted device is provided with mechanically movable valve members. These valve members are normally retained in a position within housings provided by the shunt device which maintain the valve members out of communicating relation with the blood flow through the shunt device. The valve members are provided with cooperating surfaces such as square apertures or threads which are operable to initially establish a fluid-tight communication with a hollow needle. The hollow needle is thus capable of being inserted through the skin into fluid contact with the valve member and then after such fluid coupling has been effected, the hollow needle is capable of effecting the movement of the valve member into flow communicating relation with the bloodstream.

While the patent describes the utilization of a Fogarty catheter for effecting the cleaning and declotting of the device, no provision is made for preventing the clotting of the blood within the central flow passages of the valve members when they are disposed in their normal closed positions. Moreover, while provision is made for circulating blood between the periphery of the valve members and the housing retaining the same when the valve members are in their opened position, no such provision is made for the valve members when they are in closed position and, indeed, the peripheral passages provided for continued flow when the valve members are open are themselves closed when the valve member is closed, thus presenting, along with the interior passages of the valve members, spaces where blood would be trapped and become clotted.

While it is recognized to be desirable to overcome the disadvantages of the commercially available exteriorized shunt device, the arrangement disclosed in the aforesaid patent would appear to present clotting problems equal to, if not worse than the clotting problems noted in the prior art. When it is considered that it is quite usual for cancer patients to be hypercongulable, the clotting problems of the prior art assume greater proportions when contemplating the utilization of such shunts for hyperthermic treatment of a patient for anticancer purposes. Moreover, effective hyperthermic treatments in accordance with the principles of the present invention require flow rates considerably in excess of that normally provided for kidney dialysis.

Accordingly, it is a further object of the present invention to provide a shunt device of the totally subcutaneous type which is particularly suitable for use in hyperthermic treatment of a patient for anti-cancer purposes in accordance with the present invention, which device overcomes, or at least substantially alleviates, the clotting problems of the prior art heretofore noted.

This objective is obtained by providing a totally subcutaneous implant for use with the apparatus providing the extracorporeal blood flow path, including both a blood withdrawing and a blood returning percutaneous cannula, each of which is cooperable with a trocar for effecting the percutaneous disposition thereof, which cannulas cooperate with the implant to achieve the extracorporeal blood flow. The implant comprises a body of elastomeric material adapted to be implanted totally subcutaneously in a femoral extremity, the body having an arterial passage therein, a spaced venous passage, and a bypass conduit extending from one end of the arterial passage to one end of the venous passage. An arterial tube and a venous tube of vascular prosthesis material are provided, each having one end connected in communicating relation with the other end of the respective arterial or venous passage and an opposite end adapted to be connected with a respective main femoral artery or vein side wall in communicating relation respectively with the respective interior of the femoral artery or vein.

The elastomeric body is provided with means extending from two spaced positions exterior of said elastomeric body inwardly thereof to two positions in communicating relation respectively with the arterial and venous passages operable to move in response to the insertion of a cannula-trocar assembly from (1) a closed condition excluding fluid containing space within the body between the respective two positions so that blood flowing from the arterial tube through the arterial passage will pass therefrom through the bypass conduit into the venous passage and out of said venous tube into (2) an open condition excluding fluid receiving space within the body from the exterior periphery of the portions of the respective cannula extending between the two respective positions each of which also extends percutaneously and in communicating relation with the respective arterial or venous passage so that blood flowing from the areterial tube through the arterial passage will flow through the bypass conduit as aforesaid and, in addition, will also flow into the blood withdrawing cannula (with its trocar removed), through the extracorporeal flow path, through the blood returning cannula (with its trocar removed), back into the venous passage.

A further object of the present invention is the provision of an implant device of the type described which is simple in construction, economical to manufacture and effective in operation.

Another object of the present invention is the provision of cannula-trocar assemblies particularly constructed to cooperate with such implant, which cannula-trocar assemblies are simple in construction, economical to manufacture and effective in operation.

These and other objects of the present invention will become more apparent during the course of the following detailed description and appended claims.

The invention may best be understood with reference to the accompanying drawings, wherein an illustrative embodiment is shown.

Referring now more particularly to the drawings, there is shown therein a preferred apparatus 10 embodying the principles of the present invention for practicing the method of the present invention. While it is possible to utilize other apparatus in practicing the present method, since the apparatus 10 is preferred the principles of the present invention can best be understood by first considering the preferred apparatus 10 and then considering the method procedures involved in utilizing the preferred apparatus.

In its broadest aspects, the apparatus 10 includes sterile tubing, generally indicated at 12, which defines an extracorporeal blood flow path. A pump mechanism preferably in the form of a peristaltic roller pump, generally indicated at 14, is provided for pumping blood along the extracorporeal flow path at a controlled rate from the inlet tubing end to the outlet tubing end. In addition, there is provided a temperature control zone preferably in the form of a heat exchanger assembly 16 through which the blood flowing along the extracorporeal flow path has its temperature controlled, preferably both by heating and cooling, through a control device, generally indicated at 18, for the liquid circuit of the heat exchanger assembly 16. Finally, the apparatus 10 includes means, generally indicated at 20, for communicating the inlet end of the tubing 12 defining the extracorporeal flow path with the bloodstream of a patient and the outlet end of the tubing 12 defining the extracorporeal flow path with the bloodstream of the patient, so that the returning blood is systemically distributed without adversely affecting the blood depleted areas from which the blood is withdrawn.

The tubing 12 may be formed of any suitable plastic material, as, for example, vinyl polymer (e.g. Tygon ®), polytetraflouroethylene (e.g. Teflon ®), or other plastic materials having known uses in medical applications (e.g. Silastic ®). An exemplary tubing size is ¼" i.d., with a convenient length being from 3–5'. The pump assembly 14, as previously indicated, preferably embodies a peristaltic roller type pump driven by a variable speed electric motor. A peristaltic pump is preferred because it can utilize the replaceable sterile tubing 12 for blood contact and does not provide pump parts which must be maintained in a sterile condition. An exemplary pump is manufactured by Sarns, having a 1–2 liter per minute capacity.

A preferred embodiment of the heat exchanger assembly 16 is available commercially under the tradename Travenol Mini-Prime, 5MO 337, which has a 57 cc capacity and rated flow of 1–3 liters per minute. See also U.S. Pat. No. 3,640,340, the disclosure of which is hereby incorporated by reference into the present specification.

Figure 2:
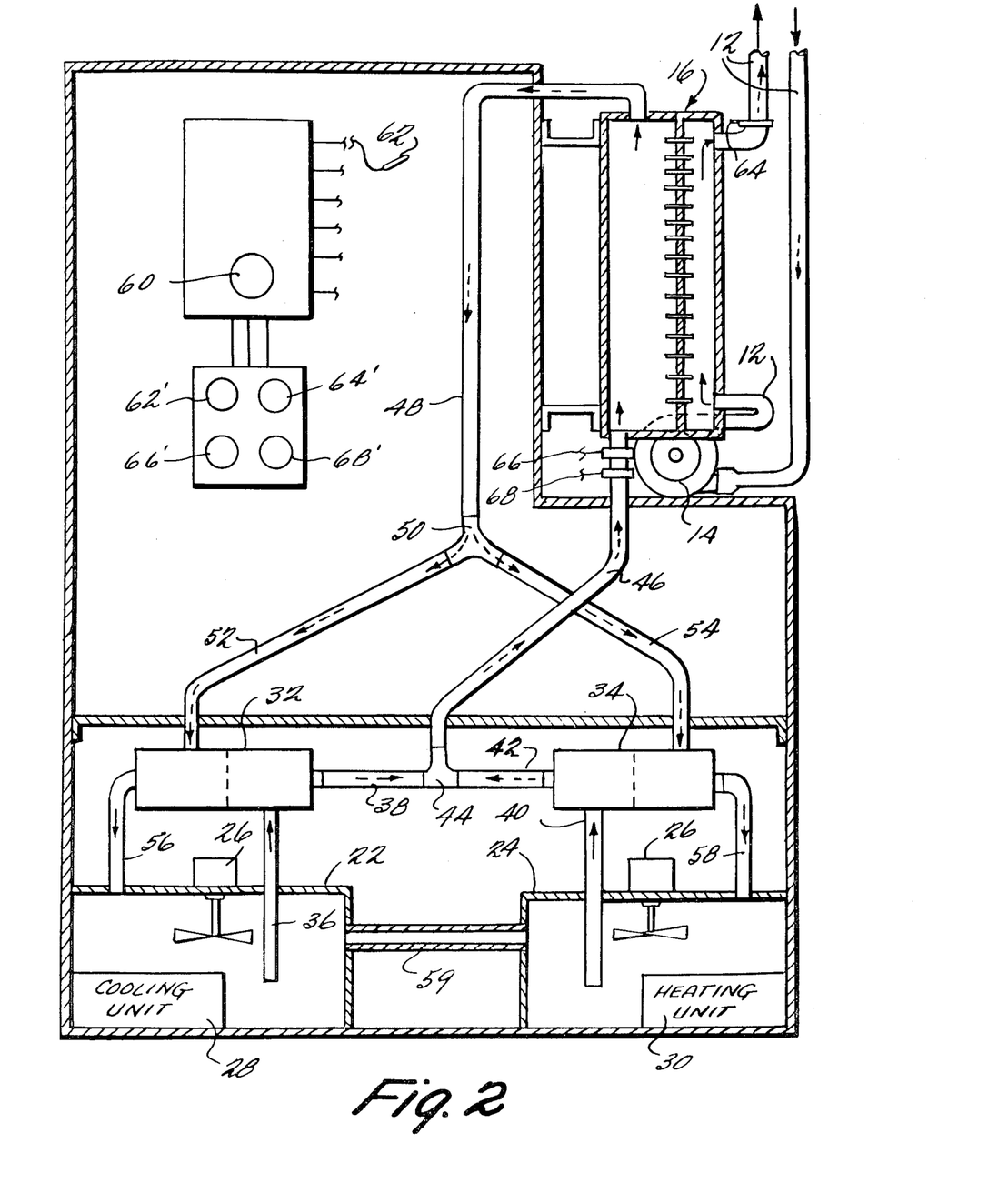
FIG. 2 is an enlarged vertical sectional view taken along the line 2—2 of FIG. 1.

With reference to FIG. 2, the control device 18 is made up of individually known components. As shown, there is provided a cooled liquid reservoir 22 and a heated liquid reservoir 24 each containing a body of liquid. While any liquid may be utilized a preferred embodiment is water. Each reservoir is provided with a stirring or agitating means 26 for purposes of mixing the liquid contained therein so as to render the temperature thereof more uniform throughout. The cool liquid reservoir 22 is provided with a cooling unit, schematically indicated at 28, while the heated liquid reservoir 24 is provided with a heating unit 30. A liquid circulating system is provided in cooperating relation between the cooled liquid reservoir 22 and heated liquid reservoir 24 and the liquid side of the heat exchanger 16. Such circulating system includes the utilization of two pump assemblies, schematically indicated in the drawings at 32 and 34.

As shown in FIG. 2, the pump assembly 32 is associated with the cooling liquid reservoir 22 and includes an inlet or suction pipe 36 extending from the reservoir 22 to one side of the pump 32 and an outlet pipe 38 extending therefrom. Similarly, an inlet pipe 40 extends from the heated liquid reservoir 24 to one side of the pump 34 which side has an outlet pipe 42 extending therefrom. Outlet pipes 38 and 42 are interconnected by a T-connector 44 which has a pipe 46 extending therefrom to the liquid inlet side of the heat exchanger 16. A pipe 48 extends from the outlet of the liquid side of the heat exchanger 16 which by means of a Y-connection 50 communicates with two branch conduits 52 and 54 extending respectively to the opposite sides of the pumps 32 and 34. The circuit is completed by pipes 56 and 58 connected respectively to the outlet of the opposite sides of pumps 32 and 34 and the cooled liquid reservoir 22 and heated liquid reservoir 24 respectively. As shown, an overflow pipe 59 is connected between the reservoirs.

The cooling unit 28 is of conventional nature and is adapted to maintain the liquid in the reservoir 22 at a substantially constant temperature as, for example, 30° C. Likewise, the heating unit 30 is of conventional construction and is adapted to maintain the liquid within the heated liquid reservoir 24 at a substantially constant temperature as, for example, 45° C. Pump 32, when operated, serves to meter from the reservoir 22 through pipe 36 an amount of liquid which is equal to the amount of liquid returned through pipe 56. In a similar manner, pump 34 when operated serves to meter an amount of flow from the reservoir 24 which is always equal to the amount returned through return pipe 58. A control, schematically indicated at 60, for varying the rate of movement of the pumps 32 and 34, e.g. electrical controls for the variable speed electrical motors driving the same which form a part of the pump assemblies schematically illustrated is operable so that the total output of the two pumps is adjusted to and maintained at a substantially constant rate, as for example, approximately 10 liters per minute. The control 60 is also operable to effect a proportional variation in the rate which each of the two pumps assume of this total output from 0–10 to 10–0.

Control of the pump assemblies 32 and 34 is undertaken in accordance with the readout of three temperature recording devices 62, 64 and 66 placed respectively to sense the core temperature of the patient's body (e.g. a rectal probe or isophageal probe), the temperature of the blood leaving the heat exchanger 16 being returned to the patient and the temperature of the liquid entering the heat exchanger. A pressure sensing device 68 is also provided in the liquid inlet line 46. It will be understood that the temperature sensing devices and pressure sensing devices are of any conventional design, preferably of the type providing a remote readout, as schematically indicated by corresponding primed numerals.

For illustrative purposes it is sufficient to note that control 60 can be manually operated to determine the proportion of the total liquid flow through the heat exchanger which is provided by the cooled liquid at 30° C. and the heated liquid at 45° C. Control 60 thus serves to directly vary the liquid temperature sensed by device 66 between the low limit of 30° C. and upper limit of 45° C., which in turn will vary the temperature of the blood sensed by device 64 which in turn will affect the patient's systemic blood temperature and hence the temperature sensed by device 62. It will be understood that while the operation of control 60 is set forth for illustrative purposes as being manual, the control 60 may be rendered automatic and programmable if desired.

Figure 3:
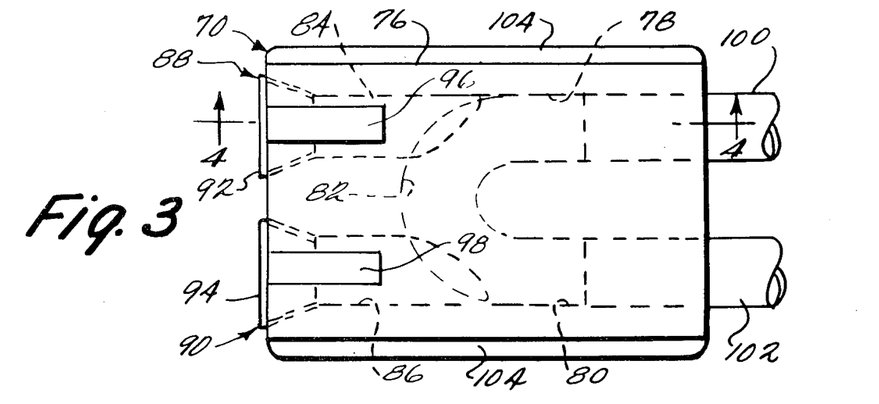
FIG. 3 is a plan view of the implant part of the apparatus.

Referring now more particularly to FIGS. 3-11, the communicating means 20 preferably comprises a totally subcutaneous implant device, generally indicated at 70, which serves as the means communicating with the patient's bloodstream and a pair of percutaneous cannula-trocar assemblies, generally indicated at 72 and 74, which serve as the means for operatively communicating the implant device 70 with tubing 12 defining the extracorporeal flow path. As best shown in FIGS. 3-7, the implant device includes a body 76 of elastomeric material such as Silastic ®, molded so as to provide an arterial passage 78, a spaced venous passage 80 and a by-pass conduit 82 connected between the inner end of the passage 78 and the inner end of the passage 80. As best shown in FIG. 3, the passages 78 and 80, together with the by-pass conduit 82, are of generally U-shaped configuration.

Each of the passages 78 and 80 has a peripheral cross-sectional configuration which is elongated in one direction; namely, the direction in which they are spaced apart, with sharp points defining opposite ends in the direction of elongation. The preferred configuration shown is further characterized by a pair of convexly curved lines extending between the sharp points, the distance between the central portions of the convex lines being approximately one-half the distance between the two end points. While the by-pass conduit may be of other cross-sectional configuration, as shown, it too is of similar cross-sectional configuration. This preferred cross-sectional configuration for the passages 78 and 80 is provided for the purpose of cooperatively receiving the correspondingly shaped exterior peripheries of the cannulas of the assemblies 72 and 74, which assemblies are so shaped for the purpose of cooperating with a pair of slits 84 and 86 formed in the body 76 in operative association with the passages 78 and 80 respectively.

Figure 4:
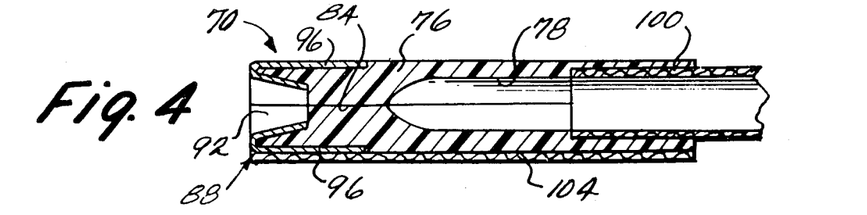
FIG. 4 is a longitudinal section taken along the line 4—4 of FIG. 3.
Figure 5:
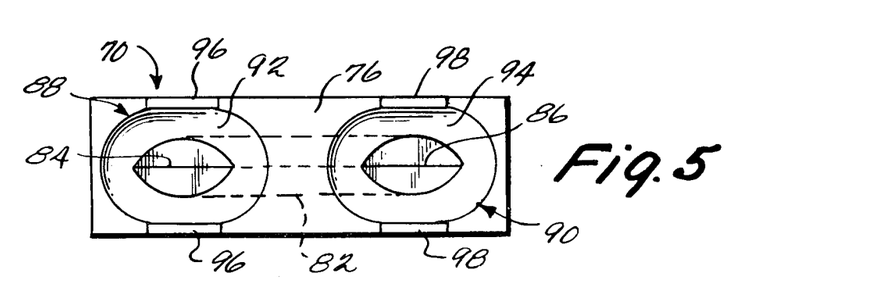
FIG. 5 is an end view of the implant shown in FIG. 3.
Figure 6:
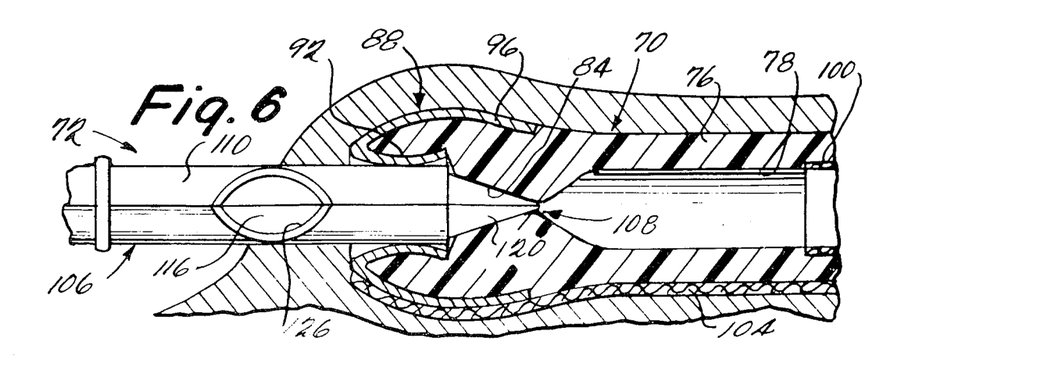
FIG. 6 is an enlarged, fragmentary sectional view illustrating the entry of the blood withdrawing cannula with its cooperating trocar assembled therein into cooperating relation with the implant and specifically the arterial passage thereof.

As shown, each slit 84 and 86 extends from a position exterior of the body 76 to a position of communication with the inner end of the associated passage 78 or 80. The width of each slit is generally equal to the distance between the end points of the associated passage and is oriented in its closed condition, as best shown in FIG. 4, in longitudinal alignment with a plane passing between the end points of the associated passage.

In the closed condition shown, the two planar interior surfaces of the body 76 which define the respective slit 84 or 86 are resiliently urged into engagement by the elastomeric characteristics of the body material. The engagement of the surfaces serves to exclude any spaces which could contain fluid such as blood between the two positions of extent of the slit, as aforesaid.

The resiliency of the elastomeric material of the body 76 also permits each slit 84 and 86 to be moved by its respective cannula-trocar assembly 72 and 74 into an open condition where the planar body surfaces defining the slit are spread arcuately so that the profile thereof coincides with the peripheral configuration of the associated passage 78 or 80.

To aid the entry and insertion of each cannula-trocar assembly through its associated slit, there is molded in embedded relation within the body 76 a pair of metallic guide structures 88 and 90. Each guide structure is preferably made of a medically acceptable interior use metal, such as stainless steel (e.g. Vitallium Metal manufactured by Howmedica). The guide structures include similar inwardly tapering annular parts 92 and 94 respectively fixed to the exterior end face of the body 76 and similar parallel spring finger parts 96 and 98 respectively embedded in the exterior of the body on opposite sides of associated slit. The tapered parts 92 and 94 provide the guide assist function previously noted while the spring finger parts 96 and 98 provide a spring assist function for the slits of the elastomeric body serving to resiliently urge the slit defining surfaces toward one another in addition to the spring function provided by the elastomeric characteristics of the material of the body 76.

Figure 1:
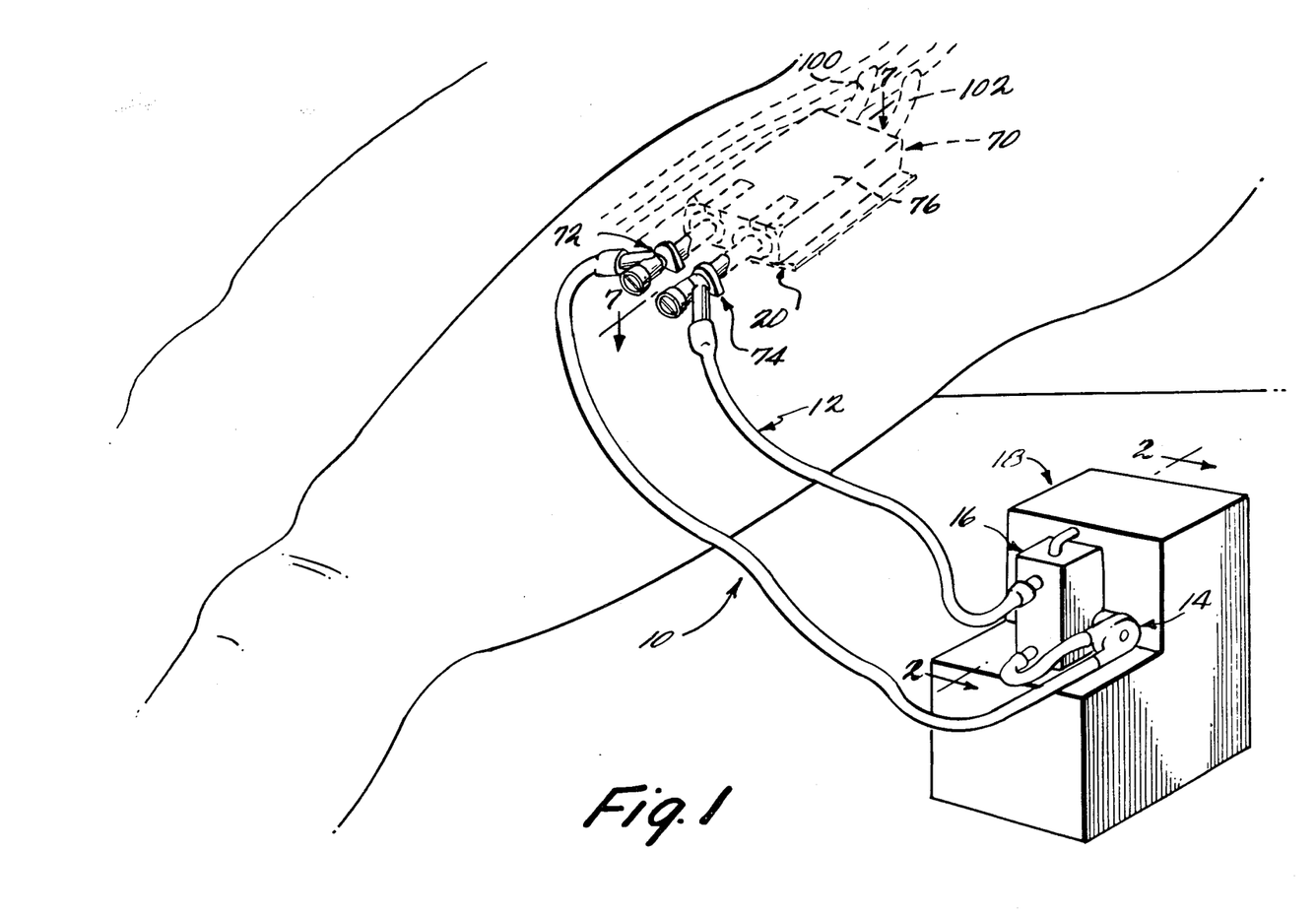
FIG. 1 is a perspective view illustrating the method and apparatus embodying the principles of the present invention.

The implant device 70 also includes a pair of tubes 100 and 102 made of vascular prosthesis material. A preferred vascular prosthesis material is woven Dacron ® marketed commercially by Meadox Medicals although any other acceptable vascular prosthesis material may be utilized. As best shown in FIG. 1, the tube 100 has one end thereof fixed in communicating relation with the outer end portion of the arterial passage 78, as by being molded in embedded relation. The opposite end of the tube 100 is adapted to be connected, as by suture, to a surgical opening formed in the side wall of a femoral artery so that the interior of the tube 100 is in communicating relation with the interior of the femoral artery. In a like manner, one end of the tube 102 is embedded in communicating relation with the outer end portion of the venous passage 80 and its opposite end is adapted to be sutured to a surgical side wall opening in the associated femoral vein so that its interior is in communicating relation with the interior of the femoral vein.

The implant device 70 also includes a layer of fabric 104 which is fixed to the inner side wall of the elastomeric body as by Silastic ® glue or the like. The fabric 104 includes marginal portions extending laterally outwardly from the operative inner side wall of the body 76 to which it is fixed. The fabric layer 104 and particularly the marginal portions thereof provide for initial fixation by suture of the body 76 during implant and for subsequent semi-permanent fixation by tissue ingrowth. A preferred fabric material is Dacron ® double velour which is marketed commercially by Meadox Medicals.

For identification purposes directly from the implant device itself, radiopaque identification (not shown) is provided on the operative outer side wall of the elastomeric body 76. Such identification insures that the proper cooperating cannula-trocar assemblies 72 and 74 will always be used since such assemblies can be ascertained from the implant itself after total implantation has been effected through X-ray identification.

Referring now more particularly to FIGS. 8-11 of the drawings, the details of construction of the cannula-trocar assemblies 72 and 74 are shown therein. It will be understood that since the assemblies 72 and 74 are left and right hand mirror images of one another, a description of one of the assemblies will suffice to give an understanding of both. The assembly 74 is shown in assembled condition in FIG. 8 and includes a percutaneous cannula, generally indicated at 106 and a cooperating trocar, generally indicated at 108.

The cannula 106 includes a tubular body which includes a straight section 110 defining the subcutaneous end portion of the cannula and an angular section 112 which, together with an adjacent part of the straight section 110, defines the extracorporeal end portion of the cannula. The cannula 106 is preferably molded of radiopaque plastic material having sufficient rigidity to prevent interior collapse when in operative position within the implant device 70. Thermoset plastics are preferred although thermoplastic materials with sufficient functional rigidity and heat stability for sterilization can be used. An exemplary material is ethylene-propylene-terpolymer (e.g. where the third monomer is norbornadiene) impregnated with a radiopaque material such as barium sulfate.

As shown, the entire straight section 110 of the cannula 106 has its exterior periphery formed with a cross-sectional configuration which conforms with and engages within the interior periphery of the body 76 defining the artery passage 78 or venous passage 80. Such configuration, however, is required only in the extent of the subcutaneous end portion which is disposed within the passage and associated slit of the implant body during operation.

The cannula 106 includes an interior passage 114 which extends through the angular section 112 into the straight section 110 and out of the extremity thereof. In order to maximize the interior passage cross-sectional area for an optimum exterior cross-sectional size, the cross-sectional configuration of the interior passage 114 at least in the straight section 110, conforms to the exterior cross-sectional configuration.

In this regard it will be noted that the trocar 108 consists essentially of a molded body of plastic material, similar to the plastic material of the cannula 106, which provides a blade part 116 and a handle part 118. The blade pat 116 is of a longitudinal extent generally equal to the longitudinal extent of the straight section 110 of the cannula 106. The main extent of the blade part 116 has an exterior peripheral cross-sectional configuration conforming with the interior cross-sectional configuration of the portion of the interior passage 114 extending through the straight cannula section 110. The blade part 116 includes a sharpened tip portion 120 which tapers gradually in cross-sectional configuration outwardly from the aforesaid configuration to a point.

It will be noted that the extracorporeal end of the straight section 110 of the cannula 106 is closed as by a diaphragm or plug of elastomeric material 122 which preferably is preslit (although may be imperforate) to permit the passage of the trocar 108, pointed end 120 first, therethrough.

The exterior periphery of the outer end of the angular section 112 is provided with gripping flanges 124 operable to effect a fluid-tight connection with the interior of the tubing 12. When the trocar 108 is withdrawn, the elastomeric plug slit, which has expanded to receive the trocar, contracts to close the end of the straight section of the cannula and insure that all of the blood will flow outwardly through the angular section 112 and into the tubing 12.

Figures 7, 11:
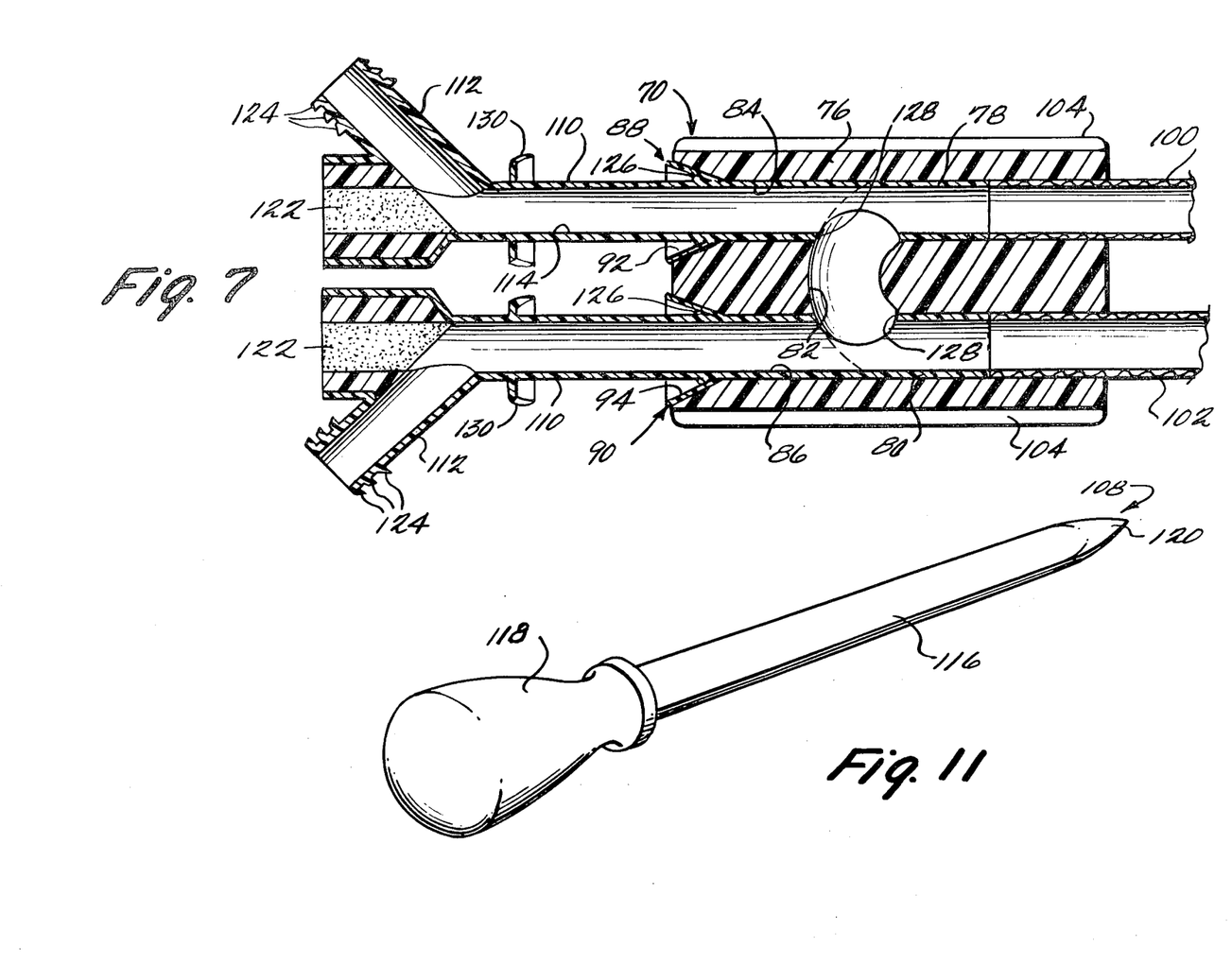
FIG. 7 is an enlarged fragmentary sectional view taken along the line 7—7 of FIG. 1.
FIG. 11 is a perspective view of the trocar shown in FIG. 8.
Figure 8:
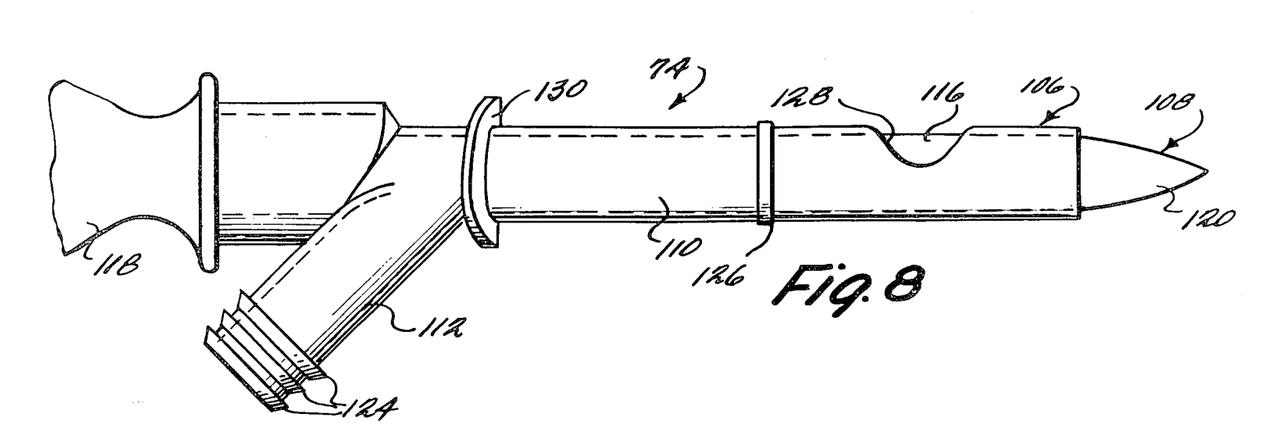
FIG. 8 is a top plan view of the blood withdrawing cannula with its cooperating trocar assembled therein.
Figure 9:
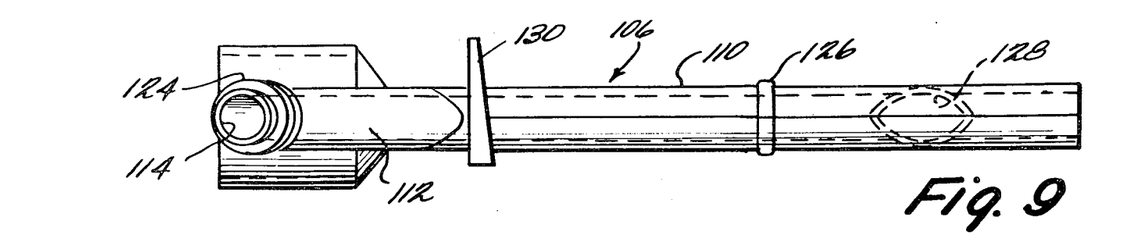
FIG. 9 is a side view of the cannula shown in FIG. 8.
Figure 10:
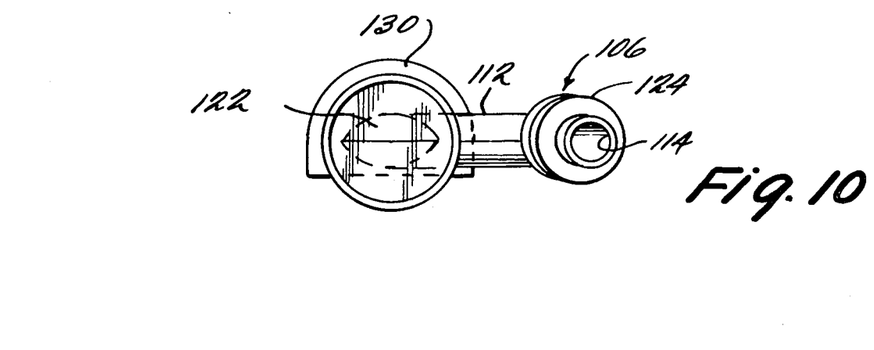
FIG. 10 is an end view of the cannula shown in FIG. 8.

Formed on the exterior periphery of the straight section 110 of the cannula is an annular shoulder 126 which forms a stop surface facing in a direction toward the open extremity of the straight cannula section operable to engage the guide part 92 or 94 of the implant device when the cannula is in its fully inserted operative position, as shown in FIG. 7. The straight cannula section 110 is formed with an opening 128 which extends inwardly from one exterior end point into communication with the interior passage 114 at a position to register with the by-pass conduit 82 of the implant body 76 when the cannula is fully inserted, as aforesaid. Formed on the exterior periphery of the extracorporeal portion of the straight cannula section 110 is a stabilizing shield 130 which facilitates maintenance of the cannula on the patient when in operative position.

A preferred procedure is to coat all of the blood contacting surfaces of the cannulas 106 (i.e. interior passages 114) tubing 12 and elastomeric body 76 (passages 78 and 80, conduit 82 and slits 84 and 86) with an anticoagulant coating. A suitable coating material for this purpose is marketed commercially under the tradename TDMAC®.

The manner in which the device 70 is surgically implanted is in accordance with usual implant procedures well known to those skilled in the art. For present purposes suffice it to say that the elastomeric body 76 is implanted in an anterior femoral region spaced downwardly from the position of bending at the hip approximately the distance of the width of a normal-sized palm (approximately 4") as is clearly shown in FIG. 1. The large area faces of the body 76 are preferably disposed parallel with the skin with the face having the fabric 104 fixed thereto innermost. The arterial and venous tubes 100 and 102 extend upwardly and the free ends are tapered and sutured to surgical openings in the side walls of the femoral artery and vein respectively so as to extend therefrom at an angle of approximately 45°. This procedure is accomplished in accordance with usual practices relating to the use of vascular prosthesis material.

The marginal edge portions of the fabric 104 are sutured to the adjacent tissue to provide initial body 76 fixation, as aforesaid. All of the exterior surfaces of the implant device 76 are contacted with tissue including tapered guide parts 92 and 94 (with fat).

As previously indicated, it is possible to use known shunt devices (e.g. U.S. Pat. No. 3,713,441) in lieu of the device 70 so long as they provide the necessary capacity which is ordinarily not the case without modification.

The advantages of the use of the implant device 70 is that it is specifically intended for long-term surgical implantation in the thigh of cancer patients, whereby its anastomosis to the femoral artery and vein, creates a high-flow (1–2 liters per minute) arteriovenous conduit which may be repeatedly entered by percutaneous insertion of the cannula assemblies 72 and 74.

As compared with other prosthetic partially exteriorized A-V Shunt devices as used for renal hemodialysis the implant device 70 reduces the risk of infection, reduces the risk of thrombosis, reduces the risk of disruption and improves the esthetics of normal usage. The renal dialysis experience indicates that partially exteriorized lower extremity shunts frequently develop infection along the tract of the shunt tubing. The incidence and severity of this type of infection would be increased in cancer patients by the immunosuppressive effects of malignancy, and the chemotherapy and radiotherapy they frequently receive. The implantable device 70 greatly diminishes the risk of infection and requires no increase in the amount of surgery needed for insertion. Cancer patients have a state of hypercoagulability or increased tendency to form blood clots in their normal and any artificial circulations. Ordinary A-V shunts last only 2–6 months in hypocoagulable dialysis patients, and likely will clot much sooner in those with the "Sticky blood" of disseminated malignancy The implantable device 70 has a shorter fluid path, much of which will be covered by a patient's own intravascular tissues, and hence will be less likely to thrombose. Partially exteriorized shunts have press connections which may be inadvertently loosened or disconnected. Such events have caused deaths in dialysis patients but, in general, those shunts are small and a patient can control a bleeding shunt before exsanguination occurs. However, disruption of the large shunt necessary for hyperthermia would result in massive bleeding, which could render a patient unconscious even before the shunt could be reached through normal clothing. This cannot happen with the device 70 as the connections are permanent, as well as totally protected.

Unlike commercially known shunts, there is no external tubing associated with the device 70. A normal bath or shower could be taken by the implanted patient, whereas those with partially exteriorized shunts cannot submerge them and must resort to less hygienic methods, a probable factor in their increased incidence of infections. Furthermore, the device 70 does not interfere with clothing or require any sort of dressing, leaving a patient's appearance unimpaired, an important asset to the depressed cancer patient.

The manner in which each cannula assembly 72 or 74 is inserted into cooperating relation to the implanted device 70 should be apparent from the above. It is of significance to note the advantages of the utilization of a main implant body 76 which provides increased palpation facility during cannulation. Moreover, cannulation is effected in a straight line relationship resulting in a straight line percutaneous cummunication with the extracorporeal flow path. The preferred cross-sectional configuration of the cannula enables simple but effective alignment to be accomplished during insertion. Such cross-sectional configuration also provides optimal cooperation with the slit 84 and 86 of the elastomeric body 76 both in expanding the slits during insertion and in contracting the peripheral portion of the cannula extending therethrough to insure a good fluid-tight connection. The extension of this cannular cross-sectional configuration with the elastomeric body passages 78 and 80 also insures non-distortion of these passages and a full flow area of 4 mm or larger.

The flow capacity provided is of extreme importance since it is a critical determining factor in the time required to bring the patient's blood up to the desired treatment temperature and to the sensitivity of the temperature control available. The approximate 1 liter minute capacity provided is based upon the average size of an average adult patient and, of course, should be varied to suit the particular size of the patient being treated. The term approximately 1 liter per minute is therefore intended to comprehend within its meaning such variation to suit the patient size.

It will be understood that once the inlet and outlet ends of the tubing 12 are connected over the flanges 124 of the cannula of the assemblies 72 and 74 and the associated trocars 108 of the assemblies are withdrawn, pump 14 can be started to commence the flow of blood along the extracorporeal flow path at the approximate 1 liter per minute as aforesaid and through the temperature control zone thereof. Initially, control 60 is set to pass 100% 45° C. water through the heat exchanger 16. During this initial treatment phase withdrawn blood temperatures measured at 62' will show a gradual increase from the initial normal reading of approximately 37° C. The capacity and effectiveness of the heat exchanger 16 is such that readings of the returning blood taken at 64 closely approximate the 45° C. maximum water temperature utilized. As the heated blood is returned to the femoral vein through the blood receiving percutaneous cannula 106, venous passage 80 and tube 102, it is distributed systemically which in turn, has the effect of increasing the total systemic temperature. As the patient's core body temperature increases toward the 41.5° C. level control 60 must be operated to lower the liquid reading at 66 to a value below 45° C. as, for example, 42.5° C. The liquid temperature level stabilized at 42.5° C., the patient core body temperature readings at 62, and returning blood readings will stabilize at a desired level of approximately 41.5° C. and 40.0° C. respectively. This critical phase wherein the patient's systemic temperature is increased and stabilized should, as aforesaid, normally be completed within one hour, although here again, variation because of patient size will occur.

Once temperature stabilization is achieved as aforesaid, treatment is continued for a time period effective for the particular cancer which the patient has. A preferred minimum time for all types including simple carcinomas is six hours although treatment times of 20 hours and longer will be required for more complex cancer situations.

Preferably, a third phase of the present method involves utilizing the continued blood flow through the temperature control zone of the extracorporeal flow path to reduce the blood temperature to normal and, hence, the patient's systemic temperature to normal. This phase is initiated by turning control 60 to pass predominately 30° C. water through the heat exchanger 16. This has the effect of substantially lowering the readings of the returning blood taken at 64. Again, this cooler blood is distributed systemically, causing the systemic temperature to lower until a normal of 37° C. is reached. The decreasing temperature phase normally will require a time period approximately the same as the initial increasing temperature phase although usually somewhat less.

Preferably, the patient is maintained during treatment in a skin contacting environment approximating that of an intensive care room. While it is within the contemplation of the invention to provide a skin insulating environment and even comparable elevated temperatures to inhaled gases, the intensive care like environment is preferred because the temperature level of the skin and respiratory system does not vary significantly from the induced hyperthermia systemic level and access to the patient is much more readily obtained. Moreover, the application of radiation or chemotherapy treatments can be carried on simultaneously if desired.

It thus will be seen that the objects of this invention have been fully and effectively accomplished. It will be reailized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. A totally subcutaneous implant for use with an apparatus providing an extracorporeal blood flow path extending from a blood withdrawing percutaneous cannula cooperable with said implant to a blood returning percutaneous cannula cooperable with said implant, which blood flow path has a capacity of maintaining a minimum flow rate of approximately 1 liter per minute, said implant comprising:

a body of elastomeric material adapted to be implanted totally subcutaneously in a femoral extremity, means in said body defining an arterial passage, a spaced venous passage, and a bypass conduit extending from one end of said arterial passage to one end of said venous passage, an arterial tube of vascular prosthesis material having one end connected in communicating relation with the other end of said arterial passage and an opposite end adapted to be connected with a main femoral artery side wall in communicating relation with the interior of the femoral artery, a venous tube of vascular prosthesis material having one end connected in communicating relation with the other end of said venous passage and an opposite end adapted to be connected with a main femoral vein side wall in communicating relation with the interior of the femoral vein, blood withdrawing percutaneous cannula receiving means in said elastomeric body extending from a position exterior of said elastomeric body inwardly thereof to a position in communicating relation with said arterial passage movable between (1) a closed condition excluding fluid containing space within said body between said two positions so that blood flowing from said arterial tube through said arterial passage will pass therefrom through said bypass conduit into said venous passage and out of said venous tube and (2) an open condition excluding fluid receiving space within said body from the exterior periphery of the portion of a blood withdrawing cannula extending between said two positions which also extends percutaneously and in communicating relation with said arterial passage so that blood flowing from said arterial tube through said arterial passage will flow through said blood withdrawing cannula at a minimum rate of approximately 1 liter per minute and said bypass conduit, and blood returning percutaneous cannula receiving means in said elastomeric body extending from a position exterior of said body inwardly thereof to a position in communicating relation with said venous passage movable between (1) a closed condition excluding fluid containing space within said body between the associated two positions of extent thereof so that blood flowing from said bypass conduit will pass therefrom into said venous passage and out of said venous tube, and (2) an open condition excluding fluid receiving space within said body from the exterior periphery of the portion of a blood returning cannula extending between the associated two positions of extent thereof which blood returning cannula also extends percutaneously and in communicating relation with the venous passage so that said venous passage will receive blood flowing both from said blood returning cannula at a minimum rate of approximately 1 liter per minute and said bypass conduit.

2. An implant as defined in claim 1 wherein said arterial passage, said by pass conduit and said venous passage are of generally U-shaped configuration.

3. An implant as defined in claim 2 wherein said blood withdrawing cannula receiving means comprises opposed interengageable surfaces defining a slit in said body extending between the two positions associated therewith and said blood returning cannula receiving means comprises opposed interengageable surfaces defining a slit in said body extending between the two positions associated therewith.

4. An implant as defined in claim 3 wherein the inner portion of said arterial passage has a peripheral cross-sectional configuration which is elongated in one direction with sharp points defining opposite ends thereof in the direction of elongation and said venous passage has a peripheral cross-sectional configuration which is elongated in one direction with sharp points defining opposite ends thereof in the direction of said elongation, said slits being of a width generally equal to the distance between the end points of the associated passage and longitudinally aligned with a line extending between said end points.

5. An implant as defined in claim 3 including means associated with each slit defining a tapered guide leading to the exterior of the associated slit and means in said body associated with each slit for yieldingly urging opposed surfaces defining the associated slit together.

6. An implant as defined in claim 5 wherein said body of elastomeric material has fabric portions extending from the exterior thereof for enabling said body to be initially fixed by suture and subsequently semipermanently fixed by time ingrowth.

7. An implant as defined in claim 6 wherein said fabric is polyester double velour.

8. An implant as defined in claim 3 including means in said body associated with each slit for yieldingly urging the opposed surfaces defining the associated slit together.

9. An implant as defined in claim 1 wherein said body is provided with radiopaque identification.

10. An implant as defined in claim 1 wherein the vascular prosthesis material of each of said tubes is woven polyester.

11. An implant as defined in claim 1 wherein said body of elastomeric material has fabric portions extending from the exterior thereof for enabling said body to be initially fixed by suture and subsequently semipermanently fixed by tissue ingrowth.

12. An implant as defined in claim 11 wherein said fabric is polyester double velour.

13. A totally subcutaneous implant for use with an apparatus providing an extracorporeal blood flow path extending from a blood withdrawing percutaneous cannula cooperable with said implant to a blood returning percutaneous cannula cooperable with said implant, said implant comprising:

a body of elastomeric material adapted to be implanted totally subcutaneously in an extremity, means in said body defining an arterial passage, a spaced venous passage, and a bypass conduit extending from one end of said arterial passage to one end of said venous passage, an arterial tube of vascular prosthesis material having one end connected in communicating relation with the other end of said arterial passage and an opposite end adapted to be connected in communicating relation with the interior of an extremity artery, a venous tube of vascular prosthesis material having one end connected in communicating relation with the other end of said venous passage and an opposite end adapted to be connected in communicating relation with the interior of a vein, means in said elastomeric body extending from a position exterior of said body inwardly thereof to a position in communicating relation with said arterial passage movable between (1) a closed condition excluding fluid containing space within said body between said two positions so that blood flowing from said arterial tube through said arterial passage will pass therefrom through said bypass conduit into said venous passage and out of said venous tube and (2) an open condition excluding fluid receiving space within said body from the exterior periphery of the portion of a blood withdrawing cannula extending between said two positions which also extends percutaneously and in communicating relation with said arterial passage so that blood flowing from said arterial tube through said arterial passage will flow through said blood withdrawing cannula and said bypass conduit, and means in said elastomeric body extending from a position exterior of said body inwardly thereof to a position in communicating relation with said venous passage movable between (1) a closed condition excluding fluid containing space within said body between the associated two positions of extent thereof so that blood flowing from said bypass conduit will pass therefrom into said venous passage and out of said venous tube, and (2) an open condition excluding fluid receiving space within said body from the exterior periphery of the portion of a blood returning cannula extending between the associated two positions of extent thereof which blood returning cannula also extends percutaneously and in communicating relation with the venous passage so that said venous passage will receive blood flowing both from said blood returning cannula and said bypass conduit.

14. In apparatus providing an extracorporeal blood flow path, the improvement which comprises a totally subcutaneous implant for connection with an artery and a vein of a patient and outlet and inlet assemblies cooperable with said implant for establishing communication with said implant so as to direct blood from the implant to the extracorporeal flow path and blood from the extracorporeal flow path to the implant respectively, each of said outlet and inlet assemblies comprising an elongated percutaneous cannula having a subcutaneous end portion and an extracorporeal end portion, said subcutaneous end portion providing an exterior periphery having a cross-sectional configuration elongated in one direction with sharp points defining opposite ends thereof in the direction of elongation, said cannula having an interior passage extending from the extracorporeal end portion thereof to the extremity of said subcutaneous end portion and an elongated trocar including a pointed end, said trocar having an exterior periphery extending from said pointed end of a shape to enable said trocar (1) to be inserted pointed end first through said interior passage of said cannula in a direction and to an extent sufficient to position the pointed end thereof outwardly of the extremity of said subcutaneous end portion thereof and (2) to be withdrawn from said interior passage in the opposite direction, said implant comprising a body of elastomeric material adapted to be implanted totally subcutaneously in an extremity, means in said body defining an arterial passage, a spaced venous passage, and a bypass conduit extending from one end of said arterial passage to one end of said venous passage, an arterial tube of vascular prosthesis material having one end connected in communicating relation with the other end of said arterial passage and an opposite end adapted to be connected in communicating relation with the interior of an extremity artery, a venous tube of vascular prosthesis material having one end connected in communicating relation with the other end of said venous paassage and an opposite end adapted to be connected in communicating relation with the interior of a vein, outlet valving slit means in said elastomeric body extending from a position exterior of said body inwardly thereof to a position in communicating relation with said arterial passage movable between (1) a closed condition in self-sealing relation so that blood flowing from said arterial tube through said arterial passage passes therefrom through said bypass conduit into said venous passage and out of said venous tube and (2) an open condition in sealingly engaged relation with the exterior periphery of the portion of the cannula of said outlet assembly extending between said two positions which also extends percutaneously and in communicating relation with said arterial passage so that blood flowing from said arterial tube through said arterial passage will flow through said outlet assembly cannula and said bypass conduit, and inlet valving slit means in said elastomeric body extending from a position exterior of said body inwardly thereof to a position in communicating relation with said venous passage movable between (1) a closed condition in self-sealing relation so that blood flowing from said bypass conduit will pass therefrom into said venous passage and out of said venous tube, and (2) an open condition in sealingly engaged relation with the portion of the cannula of said inlet assembly extending between the associated two positions of extent thereof which inlet assembly cannula also extends percutaneously and in communicating relation with the venous passage so that said venous passage will receive blood flowing both from said inlet assembly cannula and said bypass conduit.

15. Apparatus as defined in claim 14 wherein said arterial passage, said by-pass conduit and said venous passage are of generally U-shaped configuration.

16. Apparatus as defined in claim 14 or 15 wherein the interior passage of each cannula includes a straight portion and an angularly related outlet portion, the extracorporeal end portion of each cannula including means disposed in longitudinal alignment with the straight portion of the associated interior passage for (1) enabling the insertion of the associated trocar pointed end first therethrough and into the associated interior passage, (2) enabling the associated trocar to be removed therefrom and (3) for preventing fluid flow therethrough after the associated trocar has been removed.

* * * * *